(12) United States Patent
Fortuna et al.

(10) Patent No.: US 11,931,192 B2
(45) Date of Patent: Mar. 19, 2024

(54) DIAGNOSTIC SUPPORT

(71) Applicant: Epica International, Inc., San Clemente, CA (US)

(72) Inventors: Damiano Fortuna, Rignano Sull'Arno (IT); Leonardo Manetti, Montevarchi (IT)

(73) Assignee: EPICA INTERNATIONAL, INC., San Clemente, CA (US)

( * ) Notice: Subject to any disclaimer, the term of this patent is extended or adjusted under 35 U.S.C. 154(b) by 995 days.

(21) Appl. No.: 16/094,878

(22) PCT Filed: Apr. 14, 2017

(86) PCT No.: PCT/IB2017/052168
§ 371 (c)(1),
(2) Date: Oct. 18, 2018

(87) PCT Pub. No.: WO2017/182926
PCT Pub. Date: Oct. 26, 2017

(65) Prior Publication Data
US 2019/0125282 A1 May 2, 2019

(30) Foreign Application Priority Data
Apr. 18, 2016 (IT) .................. UA2016A002689

(51) Int. Cl.
*A61B 6/04* (2006.01)
*A01K 15/04* (2006.01)
(Continued)

(52) U.S. Cl.
CPC ............ *A61B 6/0492* (2013.01); *A01K 15/04* (2013.01); *A61B 5/0073* (2013.01); *A61B 6/03* (2013.01);
(Continued)

(58) Field of Classification Search
CPC .... A61B 2090/3937; A61B 2090/3966; A61B 2090/3979; A61B 2090/3991; A61B 2503/40; A61B 5/0073; A61B 6/02; A61B 6/03; A61B 6/04; A61B 6/0492; A61B 6/487; A61B 6/508; A61B 6/5264; A61B 90/39; A61F 2005/0188; A61F 5/05816
See application file for complete search history.

(56) References Cited

U.S. PATENT DOCUMENTS 9,827,667 B2 * 11/2017 Griffith ................. B25J 9/0006
2008/0255485 A1 * 10/2008 Johnson ............... A61H 9/0078
601/149

(Continued)

FOREIGN PATENT DOCUMENTS

DE 102010011589 A1 9/2011
GB 2 364 646 * 6/2001
WO 2011/058730 A1 5/2011

Primary Examiner — Christopher L Cook
(74) Attorney, Agent, or Firm — STEPTOE LLP; Carl B. Wischhusen

(57) ABSTRACT

A diagnostic support suitable to be attached to a patient includes a band suitable to be wrapped around and tightened onto a portion of the patient corresponding to an area of interest of the patient and an air space incorporated in the band and suitable to expand so that, when the band is tightened onto the portion of the patient, the air space compresses and stiffens the portion of the patient.

14 Claims, 3 Drawing Sheets

(51) Int. Cl.
    *A61B 5/00*          (2006.01)
    *A61B 6/00*          (2006.01)
    *A61B 6/03*          (2006.01)
    *A61B 90/00*        (2016.01)
    *A61F 5/058*        (2006.01)
    *A61B 6/02*          (2006.01)
    *A61F 5/01*          (2006.01)

(52) U.S. Cl.
    CPC ............... A61B 6/04 (2013.01); A61B 6/508 (2013.01); A61B 6/5264 (2013.01); A61B 90/39 (2016.02); A61F 5/05816 (2013.01); *A61B 6/02* (2013.01); *A61B 6/487* (2013.01); *A61B 2090/3937* (2016.02); *A61B 2090/3966* (2016.02); *A61B 2090/3979* (2016.02); *A61B 2090/3991* (2016.02); *A61B 2503/40* (2013.01); *A61F 2005/0188* (2013.01)

(56) References Cited

U.S. PATENT DOCUMENTS

| | | | | |
|---|---|---|---|---|
| 2011/0116695 A1* | 5/2011 | Wollenweber | ....... | A61B 6/5288 |
| | | | | 382/131 |
| 2014/0049629 A1* | 2/2014 | Siewerdsen | ............ | A61B 34/20 |
| | | | | 348/77 |
| 2015/0305612 A1* | 10/2015 | Hunter | ................. | A61B 1/2676 |
| | | | | 600/424 |

* cited by examiner

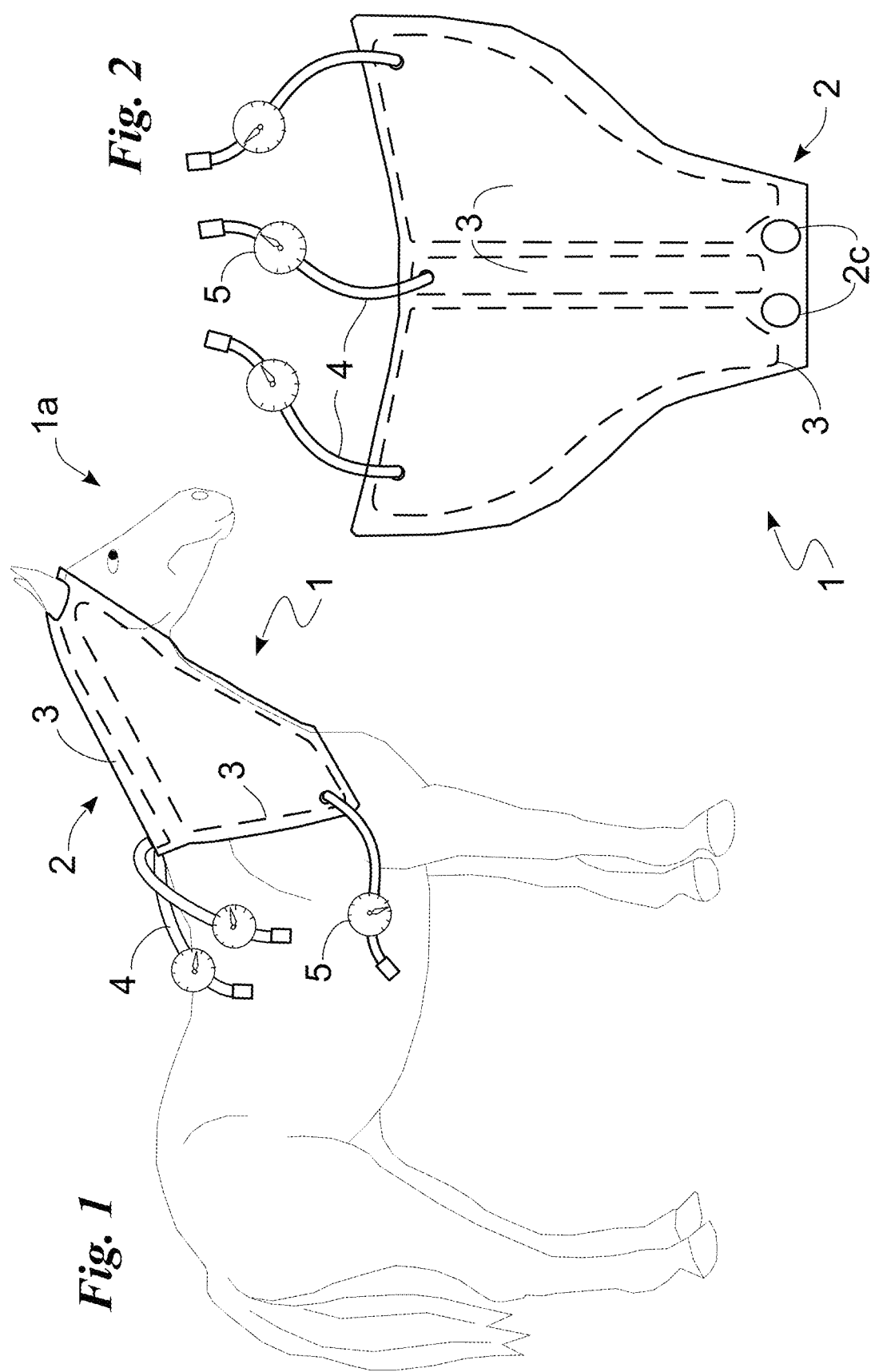

DIAGNOSTIC SUPPORT

CROSS-REFERENCE TO RELATED APPLICATIONS

This application is a National Stage Filing based on and claiming priority from International Application No. PCT/162017/052168, filed Apr. 14, 2017, which claims priority from Italian Patent Application No. UA2016A002689, filed Apr. 18, 2016, each of which is incorporated by reference in its entirety.

FIELD OF THE INVENTION

The present invention relates to a diagnostic support. In particular, the support is adapted to be used in the radiological field and applied to a patient and, suitably, an animal (more suitably a horse) during a radiological acquisition.

BACKGROUND

As is well known, one of the most important challenges when performing a radiological acquisition is to prevent the human or animal patient from moving during the radiological acquisition, which causes artifacts or other defects that impair the quality of the radiological image, making it almost impossible to perform a correct diagnosis. It should be noted that this criticality is very important in the case of tomography. In fact, tomography involves the acquisition of a sequence of images at different angles and, therefore, the combination of these acquisitions to obtain a tomographic image. Therefore, the movements of the patient lead to differences between successive acquisitions that result in defects in the tomographic image.

In order to solve these drawbacks, a first solution involves the patient lying on a bed and then blocked with restraint systems (cushions, bandages and bands). The above mentioned prior art has a few major drawbacks. A first drawback is represented by the complicated operations to block the patient with restraint systems. Another important drawback is the fact that the use of restraint systems does not allow to completely immobilize the patient who can then perform movements which, although small, may lead to considerable defects in the radiological and, in particular, tomographic image. A further drawback is the fact that the bed can exclusively be used with the patient lying.

Therefore, in recent years, radiological devices are often accompanied by optical or structured light cameras capable of detecting patient displacements during scanning. This information is used to identify and calculate the displacements of the patient and correct the radiological image.

Another drawback is that the optical and structured light cameras do not allow detection of all the movements of the patient. In particular, the cameras, by detecting only the outside profile of the patient, are not able to detect any movements of the tissues/organs or other internal movements that are not detected or detected to a very limited extent from the outside and can adversely affect the quality of the radiological image. In conclusion, the absence of information on internal displacements and, therefore, the exclusive knowledge of the movements of the outside profile allows the internal movements to be only estimated and, hence, the radiological images not to be perfectly corrected.

SUMMARY

In this context, the technical task of one embodiment of the present invention is to devise a diagnostic support which is capable of substantially obviating the above-mentioned drawbacks. Within the scope of this technical task, a major object of this embodiment is to provide a diagnostic support which allows for obtaining high quality radiological and, in particular, tomographic images. Another important object of this embodiment of the invention is to provide a diagnostic support that can be used irrespective of the position of the animal during the acquisition.

BRIEF DESCRIPTION OF THE DRAWINGS

The various embodiments of the invention will now be shown with the following detailed description of an exemplary embodiment, with reference to the attached drawings, in which:

FIG. 1 shows a diagnostic support according to an embodiment of the present invention;

FIG. 2 shows a diagnostic support according to an embodiment of the present invention;

DETAILED DESCRIPTION

Figure 3:
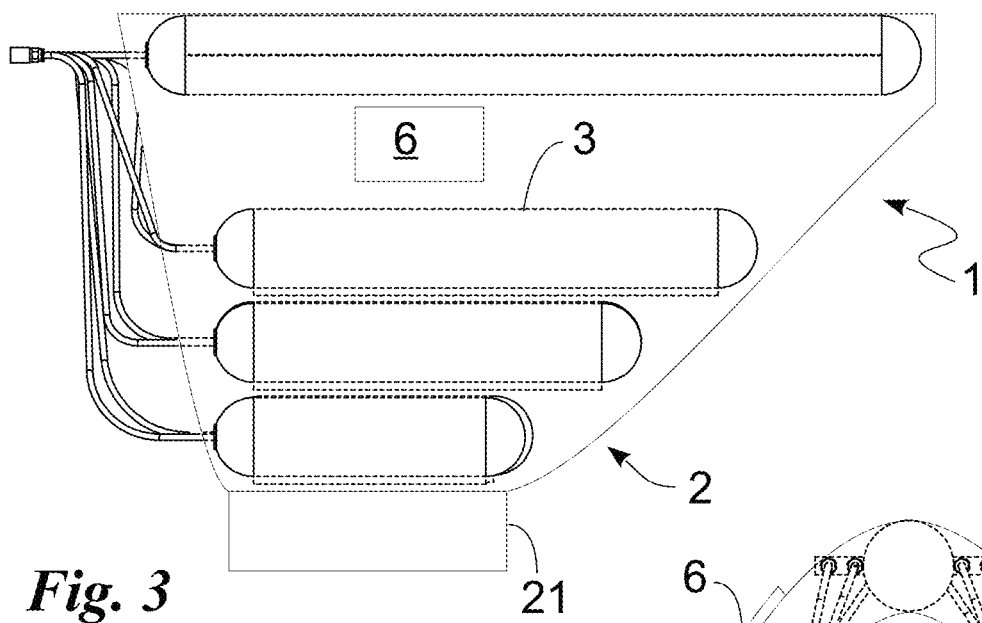
FIG. 3 is another example of a diagnostic support according to another embodiment of the present invention.
Figure 4:
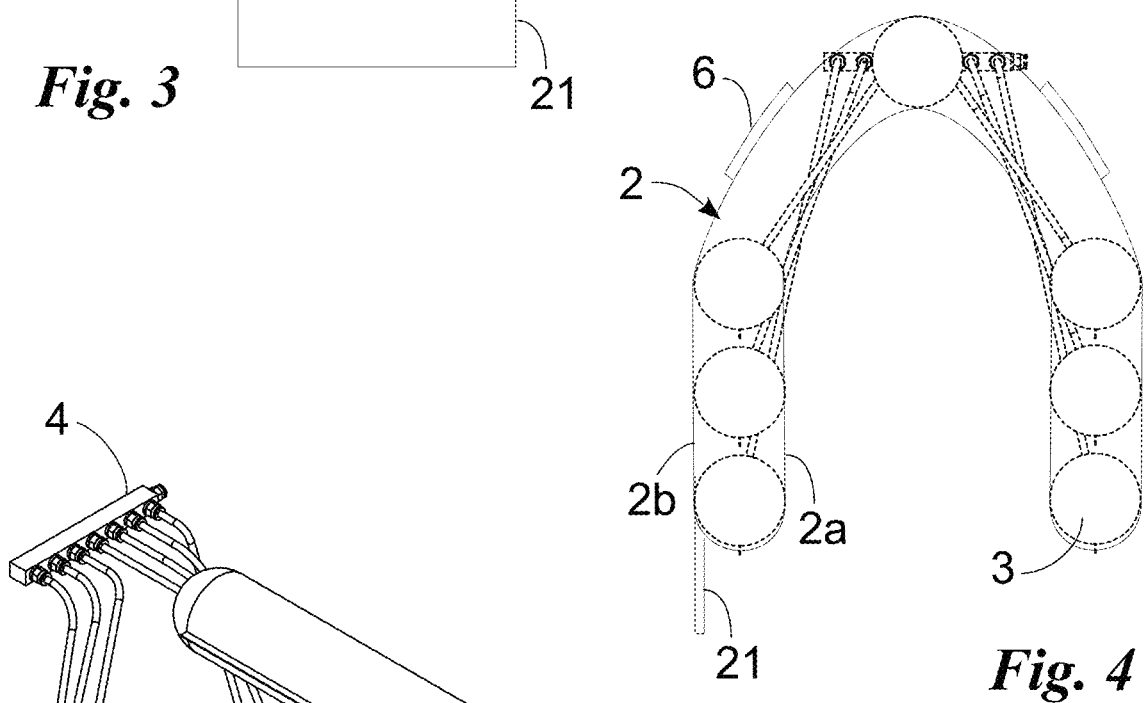
FIG. 4 shows a view of the diagnostic support of FIG. 3.
Figure 5:
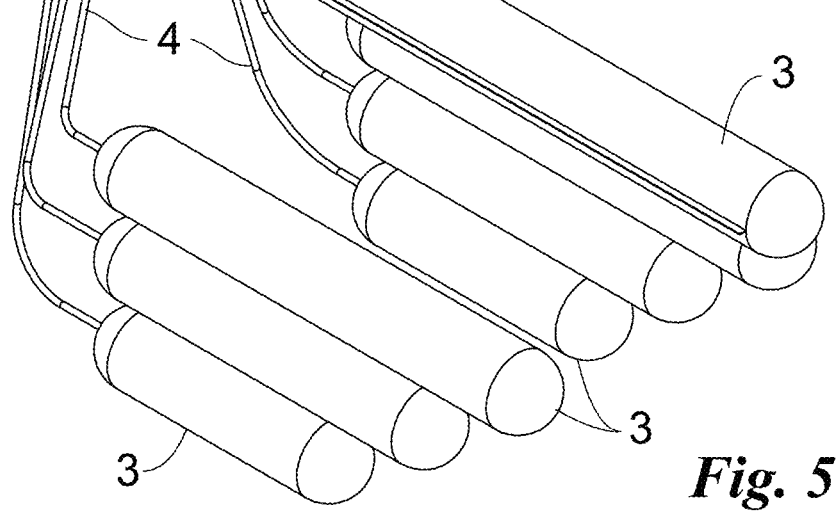
FIG. 5 is another view of the diagnostic support according to FIGS. 3-4.

In this document, the measures, values, shapes and geometric references (such as perpendicularity and parallelism), when associated with words like "about" or other similar terms such as "almost" or "substantially," are to be understood to the extent of measurement errors or inaccuracies due to production and/or manufacturing defects and, especially, unless a slight difference from the value, the measure, the shape, or the geometric reference with which it is associated. For example, these terms, if associated with a value, preferably indicate a difference of not more than 10% of the value itself.

Furthermore, when used, terms such as "first," "second," "higher," "lower," "main," and "secondary" do not necessarily identify an order, a priority relationship, or a relative position, but can simply be used to distinguish more clearly the different components from each other.

With reference to the aforementioned figures, the diagnostic support according to an embodiment of the invention, as a whole, is indicated by the numeral 1. It is suitable for use in the human or veterinary field to prevent the quality of an internal acquisition (i.e. an image reproducing the internal portion of a patient), appropriately a radiological image and, preferably, a tomography, from being impaired by any internal movements of the patient 1a at the area of radiological interest, i.e. the portion of the body to be examined. Preferably, it is adapted to stiffen the portion of the patient 1a at the area of interest so that any internal movements, instead of being absorbed by a deformation of the tissues proximal to the area, exploit the stiffness of the tissues gained thanks to the diagnostic support 1, and are transmitted and detected on the outside.

In this document, the expression "internal movements" identifies body movements, for example coming from internal organs or other anatomical parts (such as the skeleton), which usually do not (or only to a small extent) translate into skin movements.

Preferably, the diagnostic support 1 is a collar, suitably a veterinary collar (FIG. 1). Alternatively, it is a chest band, suitably a veterinary one. The diagnostic support 1 may comprise a band 2 suitable to be wrapped around and tightened onto at least one portion of a patient 1a corresponding to the area of interest. This band 2 is preferably not visible while performing the diagnostic examination and, in detail, during the radiological acquisition. It can be radiotransparent and, for example, preferably made of carbon fibre fabric. The band 2 may be elastic so that it is tensioned and, precisely, under tensile stress when in use, i.e. attached to the patient 1a at the area of interest. The band 2, when the diagnostic support 1 is in use, defines an inner surface 2a adapted to face the patient 1a and an outer surface 2b opposite the inner one 2a. The band 2 may have an open profile, and therefore comprise fastening means 21 (for example Velcro®) adapted to bind together two opposite edges of the band 2 by attaching the support 1 to the animal.

Optionally, the band 2 can be provided with one or more openings 2c adapted to facilitate the operations needed for a patient to wear the diagnostic support 1. For example, said openings 2c are adapted to allow the passage of the limbs, for example in the case of a support usable in the area of the bust, or of the ears, in the case of FIGS. 1 and 2 illustrating a diagnostic support 1 for the neck of an animal and, in detail, of a horse. The diagnostic support 1 may comprise at least one air space 3, advantageously incorporated in the band 2, and adapted to expand, varying the diagnostic support 1 so as to compress and stiffen at least the portion of the patient 1a at the area of interest, allowing at least part (preferably all) of the internal movements to be transferred to the band 2 and, therefore, to the outside, making them easily measurable as described below. In particular, it may comprise a single air space 3 capable of contacting almost at least 30% and, in detail, 50% and, in some cases, the whole portion of the patient 1a wrapped by the band 2 so as to allow the diagnostic support 1 to at least partially, and preferably totally, adapt to the body portion enclosed by the band 2. Alternatively, the diagnostic support 1 may comprise multiple, suitably three or five, air spaces 3 incorporated in the band 2 and capable of substantially contacting at least 30% and, in detail, 50% and, in some cases, the whole portion of the patient 1a wrapped by the band 2. The air spaces 3 can be isolated from one another so as not to have air passage between them and thus permit having spaces 3 with different internal pressures. Alternatively, at least part, and preferably all of the air spaces 3 are connected to each other so as to have a passage of fluid/gas between the air spaces 3, which thus substantially assume the same pressure.

The air space 3 is suitable to be arranged between the band 2 and the patient 1a when the diagnostic support 1 is in use. It may be in the area of the inner surface 2a. Accordingly, when the space 3 expands, the band 2, by being under tension/traction, forces the air space 3 to expand towards the patient 1a. As a result, the body portion enclosed by the band 2 is forced to absorb, suitably in a prevailing manner, the expansion of the air space 3, and hence contracts by stiffening so as to restrict the skeletal and muscular movements. Intimate adhesion, by virtue of the pressure of the air space 3 on the skin, makes it possible to transfer the internal movements (coming from muscles and bones) to the band 2, making them easily detectable as described below. The at least one space 3 is preferably made of a radiotransparent material, such as for example a fabric suitably made of carbon fibre, and is capable of varying its volumetric extension and, therefore, that of the diagnostic support 1 when filled with a suitably radio-transparent fluid and, in particular, with a gas, such as air.

To this end, the diagnostic support 1 may comprise one or more connectors 4 adapted to allow said fluid to exit and enter the one or more air spaces 3. In particular, the connectors 4 are adapted to connect one or more air spaces 3 to a compressed air system or other similar system for introducing said fluid into the air spaces 3.

The diagnostic support 1 may comprise at least one pressure gauge 5 adapted to measure the pressure inside one or more air spaces 3. The diagnostic support 1 may comprise at least one marker 6 adapted to be recorded during the diagnostic, specifically radiological, examination, and, conveniently, to be connected, preferably in an integral manner, to the band 2. To be precise, the marker 6 is connected, preferably in an integral manner, to the outer surface 2b so as to be visible when the diagnostic support 1 is in use. In particular, the marker 6, by being bound and, in detail, integral with the band 2, allows for easily measuring the movements of the band 2 to which, due to the stiffening caused by the one or more air spaces 3, at least part of (preferably all) the internal movements are transferred. The marker 6 can be optical, i.e. visible by an optical camera, and\or radio-opaque, i.e. visible during the radiological acquisition; and\or thermal and therefore visible with a thermographic camera. Preferably, the marker 6 can be detected both by the acquisition means described below and by the recording means described below. In particular, it can be both optical and radio-opaque. For example, it may comprise a chessboard on which radio-transparent elements suitable to be recorded, preferably exclusively, by recording means such as an optical camera, alternate with radio-opaque elements suitable to be recorded by a radiological imaging device and, suitably, by an optical camera.

Figure 6:
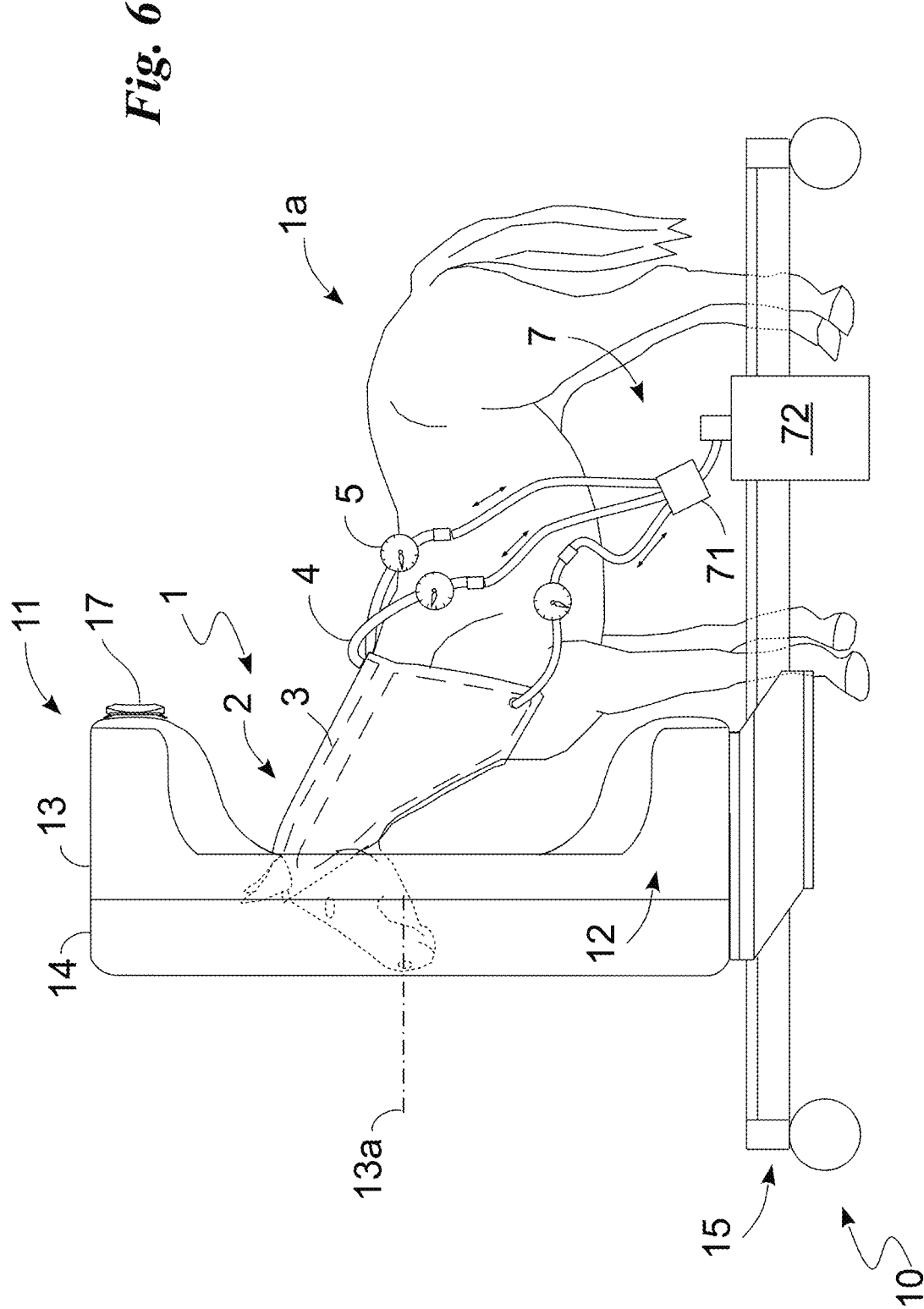
FIG. 6 sets forth the diagnostic support according to an embodiment of the present invention.

The diagnostic support 1 may comprise a filling member 7 for filling the at least one air space 3, which is adapted to be placed in fluidic connection with said air space 3 and, therefore, control its expansion by injecting a fluid into the space 3. Additionally, the filling member 7 is adapted to control its contraction, defining a fluid discharge from the air space 3. The filling member 7 may comprise at least one pump 71 suitable to control the injection and/or extraction of a fluid from each air space 3; and suitably a tank 72 for said fluid. The pump 71 can be integrated in the band 2 or structurally separated therefrom as in FIG. 6. The tank 72 can be integrated in the band 2 or structurally separated therefrom as in FIG. 6. Preferably, the filling member 7 can comprise a supply system for the pump 71 identifiable as a battery. The supply system can be integrated in the band 2 or structurally separated therefrom. Obviously, the filling member 7 can comprise conduits adapted to place the pump 71 in fluidic connection with each air space 3 and, if present, with the tank 72.

The diagnostic support 1 can be part of a diagnostic inspection device 10 (FIG. 6) adapted to perform an internal acquisition of the area of interest and, in detail, of a radiological imaging device, known per se, or of a magnetic resonance device, also known per se. The radiological imaging device may be adapted to perform a radiological acquisition, such as a radiograph, a fluoroscopy, or a tomography. In particular, the diagnostic inspection device is capable of obtaining one or more acquired, preferably radiological images, and thus provide a diagnostic image, which is preferably of the radiological and, more preferably, of the tomographic type. Examples of the diagnostic inspection device and, specifically, of radiological imaging are described in PCT/162015/055233 (from page 2, line 7 to page 57, line 23 and in FIGS. 1a-5 included for reference); in IT102016000010051 (from page 4, line 4 to page 38, line 2 and in FIGS. 1a-10 included for reference); and in IT102016000010089 (from page 2, line 7 to page 37, line 2 and in FIGS. 1a-9 included for reference). The diagnostic inspection device 10 can comprise acquisition means, which are suitably radiological, such as an X-ray source 11 and a detector 12 as described in said PCT/162015/055233, capable of acquiring the area of interest and, suitably, a rotor 13 adapted to allow the acquisition means to rotate with respect to the patient 1a around a rotation axis 13a; and preferably a stator 14 adapted to support the rotor 13 and hence the acquisition means 11 and 12; and more preferably translation means 15 for translating the rotor along a translation axis, which is suitably parallel, and in detail coinciding with said rotation axis 13a.

The acquisition means 11 and 12 are adapted to provide an internal (suitably radiological) acquisition of the area of interest by recording markers (6) and the area of interest. As a consequence, the marker 6 can therefore be visible in the image thus acquired. The diagnostic inspection device can comprise means for recording 17 the marker 6. The recording means 17 are able to record the marker 6 during the internal acquisition performed by the acquisition means 11 and 12. They can be optical and, for example, identifiable as a camera, which is suitably optical and capable of recording the marker 6 during the radiological and, in particular, the tomographic acquisition of the area of interest. The recording means 17 may be attached to the rotor 13 and, for example, located next to the acquisition means and, for example, to the source 11 (FIG. 6) and/or the detector 12. Alternatively, they can be placed on a separate structure from that of the rotor 13, such as the stator 14 or the translation means 15. The recording means 17 are able to record the marker 6 during the internal acquisition performed by the acquisition means 11 and 12.

The diagnostic inspection device may comprise a motion compensation block, which is adapted to determine the movements, suitably the internal ones, by detecting the movements of the marker 6 thanks to the recording means. The compensation block is thus able to determine the movements of the patient and, in particular, of the area of interest made during the internal acquisition and, on the basis of said movements, to eliminate the artifacts from the same internal acquisition and hence from the image obtainable therefrom. The displacements are determined on the basis of the displacements of the marker 6 calculated according to the recording performed by the recording means 17.

The operation of a diagnostic support, described above as regards structure, is as follows. The operator attaches the diagnostic support 1 to the patient 1a by placing the inner surface 2a facing the patient 1a and, in particular, by enclosing the at least one air space 3 between the band 2 and the patient 1a. It is noted that the diagnostic support 1 is attached to the patient 1a by placing the band 2 under tensile stress.

At this point, for example, by using the filling member 7, the operator injects a fluid, for example, air, into the at least one air space 3, which expands. In detail, the traction of the band 2 is discharged onto the air space 3 which is thus forced to expand towards the patient 1a. This expansion compresses the tissues, which stiffen, allowing any internal movements to be visible from the outside.

At this point, the operator drives the diagnostic inspection device 10 into the execution of the diagnostic examination (such as a radiological acquisition) and, at the same time, the recording means 17 records any movements of the marker 6. This information is thus transmitted to the motion compensation block which corrects the images on the basis of the displacements of the marker 6 and, in particular, the displacements, by zeroing. In this case, the correction may comprise calculating the displacement, correcting the acquired images, and then obtaining the diagnostic image on the basis of the corrected acquired images. In detail, the determination may require the calculation of the direction, sense, and modulus of the movements of the patient 1a between two or more acquired images (suitably between all the acquired images); the correction of the acquired images may comprise correcting the position of one or more pixels of either of the images (or alternatively of both images) on the basis of the direction, sense and modulus values just calculated.

Alternatively, the correction of the images can be made by taking into account the displacement by discarding one or more of the acquired images. In this case, the information is used to determine at least the modulus of the displacements between two or more acquired images; if this value exceeds a preset threshold, the acquired image is discarded. In a further alternative, the correction of the displacements may comprise discarding one or more of the acquired images, and then, by zeroing, the displacements of the non-discarded acquired images.

The operation of the diagnostic support described above allows for defining an innovative method for attaching a diagnostic support to a patient, which is adapted to be actuated by the aforementioned diagnostic support 1. The method of attaching a diagnostic support may comprise, initially, an attachment step in which the diagnostic support 1 is attached to the patient at the area of interest. In this attachment step, the band 2 is placed under tensile stress and, by exploiting the fastening means 21, locked on the patient. It is noted that at the end of this step the band 2 is under traction and stretched. Subsequently, the method of attaching a diagnostic support may comprise a step of expansion of the radiological support 1. In this step, a fluid, preferably a radio-transparent fluid, is injected into the one or more air spaces 3, which thus begin to expand. Due to the tension of the band 2, the air spaces 3 expand towards the patient 1a. As a result, the internal tissues proximal to the area of interest are compressed, and thus stiffened, so that any internal movements, instead of being absorbed by a deformation of the tissues proximal to the area, are transmitted to the outside thanks to the gained stiffness of the tissues. In particular, the gained stiffness of the internal tissues causes any internal movements to be transferred, at least partially (preferably totally), to the band 2, making them easy to measure. More in particular, any internal movements, due to the suitably integral connection of the marker 6 to the band 2, are transferred to the marker 6, making them extremely easy to measure even with known techniques for the detection of movements (for example an optical or structured light camera). Once the diagnostic test is completed, the method of attaching a diagnostic support may comprise releasing the support 1 in which a contraction of the air spaces 3, and therefore the disengagement of the band 2 from the patient 1a, are commanded.

The disclosed embodiments achieve significant advantages. A first important advantage is that the diagnostic support allows for substantially eliminating the defects of the radiological image caused by any internal movements. This advantage has been obtained thanks to the presence of the air spaces 3 which, by expanding, stiffen the internal tissues at the area of interest, limiting the movements. In fact, the above diagnostic support 1 performs the function of transferring, thanks to the intimate adhesion/pressure of the air space 3 on the skin of the patient, the internal movements (caused by muscles and/or bones) to the band 2 on which the marker 6 is applied. This aspect is further enhanced by the fact that the support 1 restricts the internal movements thanks to the compression forces applied by the band 2 onto the skin of the patient. This is because the compression forces stiffen the internal tissues, so that any internal movements, instead of being absorbed by a deformation of the tissues proximal to the area, exploit the stiffness of the tissues gained thanks to the diagnostic support 1, and are transmitted and thus detected on the outside.

Another advantage is thus given by the presence of the markers 6 connected to the diagnostic support 1, which allow such movements to be detected and therefore for having all the information required for attenuating the noise caused by undesired internal movements, and thus for making the radiologic image a high quality image easy to read.

Embodiments of the invention are susceptible of variations falling within the scope of the inventive concept, as specified in the independent claims, and of the related technical equivalents. In this context, all details are replaceable by equivalent elements and any type of materials, shapes and dimensions may be present.

The invention claimed is:

1. A diagnostic support suitable to be attached to a patient, said diagnostic support comprising:
    a band configured to be wrapped around and tightened onto at least one portion of said patient corresponding to an area of interest of said patient; and
    at least two air spaces incorporated in said band and configured to expand so that, when said band is tightened onto said at least one portion of said patient, said at least one air space compresses and stiffens said at least one portion of said patient so as to permit at least a part of an internal movement to be transferred to said band,
    wherein said air spaces are isolated from one another so that said air spaces are configured to have a different internal pressure, and
    wherein the patient is a horse, and the band is adapted to have two opposing portions positioned on opposite sides of a neck of the horse.

2. The diagnostic support according to claim 1, wherein said at least one air space is configured to be arranged between said band and said patient.

3. The diagnostic support according to claim 1, wherein said band is radio-transparent.

4. The diagnostic support according to claim 1, comprising at least one pressure gauge configured to measure the pressure inside said at least one air space.

5. The diagnostic support according to claim 1, comprising at least one marker connected to said band and configured to be recorded during a diagnostic examination.

6. The diagnostic support according to claim 5, wherein said marker comprises radio-transparent elements configured to be recorded by an optical camera alternating with radio-opaque elements configured to be recorded at least by a radiological imaging device.

7. The diagnostic support according to claim 1, wherein the band has an open profile and comprises:
    one or more openings through the open profile of the band adapted to allow passage of limbs of said patient; and
    a fastener adapted to bind together two opposite edges of the band to attach the band to the patient.

8. A diagnostic inspection device comprising:
    a diagnostic support configured to be attached to a patient, said diagnostic support comprising:
        a band configured to be wrapped around and tightened onto at least one portion of a patient corresponding to an area of interest of said patient
        at least one marker connected to said band; and
        at least two air spaces incorporated in said band and configured to expand so that, when said band is tightened onto said at least one portion of said patient, said at least one air space compresses and stiffens said at least one portion of said patient so as to permit at least a part of an internal movement to be transferred to said band, wherein said air spaces are isolated from one another so that said air spaces are configured to have a different internal pressure;
    acquisition means configured to perform an internal acquisition of the area of interest of said patient by recording said at least one marker and said area of interest; and
    recording means configured to record said at least one marker during said internal acquisition,
    wherein the patient is a horse, and the band is adapted to have two opposing portions positioned on opposite sides of a neck of the horse.

9. The diagnostic inspection device according to claim 8, wherein the diagnostic inspection device is a radiological imaging device or a magnetic resonance device comprising said acquisition means and configured to determine the movements of the area of interest based on movements of the marker recorded by said recording means and to eliminate artifacts of said internal acquisition based on said movements.

10. The diagnostic inspection device according to claim 8, wherein the band has an open profile and comprises:
    one or more openings through the open profile of the band adapted to allow passage of limbs of said patient; and
    a fastener adapted to bind together two opposite edges of the band to attach the band to the patient.

11. The diagnostic support according to claim 8, wherein the band is further adapted to have a central portion, between said two opposing portions, positioned on top of the neck of the horse.

12. The diagnostic support according to claim 11, wherein said at least two air spaces incorporated in said band comprise three air spaces corresponding, respectively, to said two opposing portions and said central portion.

13. The diagnostic inspection device according to claim 8, wherein the band is further adapted to have a central portion, between said two opposing portions, positioned on top of the neck of the horse.

14. The diagnostic inspection device according to claim 13, wherein said at least two air spaces incorporated in said band comprise three air spaces corresponding, respectively, to said two opposing portions and said central portion.

* * * * *